United States Patent
Pastore et al.

(10) Patent No.: US 8,118,041 B2
(45) Date of Patent: Feb. 21, 2012

(54) PLASTIC TOOTH CLEANER

(76) Inventors: Sophie Elizabeth Pastore, Stamford, CT (US); Michael Patrick Pastore, Fairfield, CT (US)

(*) Notice: Subject to any disclaimer, the term of this patent is extended or adjusted under 35 U.S.C. 154(b) by 56 days.

(21) Appl. No.: 12/799,799

(22) Filed: May 3, 2010

(65) Prior Publication Data

US 2011/0265812 A1    Nov. 3, 2011

(51) Int. Cl.
*A61C 15/00* (2006.01)

(52) U.S. Cl. ........................................ 132/329

(58) Field of Classification Search ............ 132/309, 132/321, 323, 329; 433/3, 142, 216; D28/65, D28/68; 206/104, 134, 581; *A61C 15/00*
See application file for complete search history.

(56) References Cited

U.S. PATENT DOCUMENTS

| | | | | |
|---|---|---|---|---|
| 175,794 A | * | 4/1876 | Wallace | 132/323 |
| 2,623,003 A | * | 12/1952 | Friedlob et al. | 132/321 |
| 3,511,249 A | * | 5/1970 | Baitz | 132/329 |
| 3,646,628 A | * | 3/1972 | Halford | 15/118 |
| 3,775,848 A | * | 12/1973 | Barnett | 132/329 |
| 4,974,615 A | * | 12/1990 | Doundoulakis | 132/321 |
| 5,002,077 A | * | 3/1991 | Wiley | 132/321 |
| 5,038,805 A | * | 8/1991 | Lee | 132/321 |
| 5,775,346 A | * | 7/1998 | Szyszkowski | 132/329 |
| 5,915,392 A | * | 6/1999 | Isaac | 132/200 |
| 6,012,468 A | * | 1/2000 | Huang | 132/321 |
| 6,526,993 B1 | * | 3/2003 | Wagner | 132/321 |
| 2001/0035194 A1 | * | 11/2001 | Narayanan | 132/321 |

* cited by examiner

*Primary Examiner* — Todd Manahan
*Assistant Examiner* — Tatiana Nobrega

(57) ABSTRACT

The Plastic Tooth Cleaner is a hand-held plastic device that allows a person to remove food particles from spaces between their teeth more conveniently than existing flossing techniques. It is a three inch long device, with a helical shaped body and a straight, uniformly tapered segment at each end. The device is easily held and maneuvered. The device is more pliable than a common toothpick, inexpensively produced, disposable, and is designed for use by the general public.

3 Claims, 1 Drawing Sheet

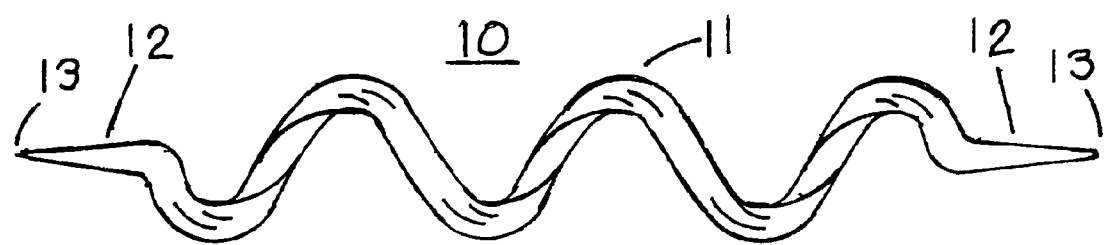

PLASTIC TOOTH CLEANER

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

BACKGROUND OF THE INVENTION

The Plastic Tooth Cleaner enables an individual to remove food particles from between the teeth. The invention is firm, but flexible enough to reach into tight spaces between close teeth.

Similar devices exist for cleaning between teeth, with notable differences.

U.S. Pat. No. 5,038,805 describes a dental floss which cleans by pulling the floss through the space between the teeth, requiring the use of both hands. By its nature, it is difficult to rotate floss to aid in the dislodging of food particles.

U.S. Pat. No. US 2001/0035194 describes a flossing tip requiring a power dental flossing device, whereas the Plastic Tooth Cleaner is completely manual and does not require any additional mechanical device in order to perform its purpose.

BRIEF SUMMARY OF THE INVENTION

The invention is a hand-held plastic device that allows the user to clean spaces between close teeth more conveniently than existing techniques or instruments. The flexible helical configuration allows for easier holding and maneuvering of the tip in order to reach difficult spaces between the teeth and requires only one hand to use effectively.

The invention has a distinct advantage over existing flossing or cleaning techniques in that it is easier to control and use and is more durable.

BRIEF DESCRIPTION OF THE SEVERAL VIEWS OF THE DRAWING

FIG. 1 is a Plan View of the plastic tooth cleaner according to the invention.

DETAILED DESCRIPTION OF THE INVENTION

FIG. 1 illustrates a preferred embodiment 10 of a tooth cleaner device according to the invention.

The invention consists of a thin piece of pliable plastic, the body 11 is approximately three (3) inches in length and approximately one-eight (⅛) of an inch in diameter, and formed into a helical configuration, with an outside diameter of three-eights (⅜) of an inch.

At both ends 12 there is a straight section, approximately three-eights (⅜) of an inch in length that tapers down to a point 13 with a diameter of approximately one-thirty second (1/32) of an inch. Either end may be used to clean the teeth.

The invention will be manufactured by extruding plastic into the shape and size described above and indicated on the drawings.

We claim:

1. A tooth cleaning device, made out of firm plastic, consisting of a helical body having a longitudinal axis where straight tapering projections extend away from each end of the helical body along the longitudinal axis of the helical body wherein said device is grasped by the helical body and rotated to maneuver the straight tapering projections into tight spaces between a user's teeth and/or gums.

2. The tooth cleaning device of claim 1 wherein said body is manufactured in a helical shape approximately two and one quarter inches (2-¼") long.

3. The tooth cleaning device of claim 1 wherein each of the straight tapering projections are manufactured with a uniform taper and taper to a diameter of approximately one-thirty-second of an inch and are approximately three-eighths of an inch in length.

* * * * *